United States Patent
Godsmark et al.

(10) Patent No.: US 8,115,042 B2
(45) Date of Patent: Feb. 14, 2012

(54) OLIGOMERISATION OF OLEFINS

(75) Inventors: John Stephen Godsmark, Grez Doiceau (BE); Georges Marie Karel Mathys, Bierbeek (BE); Paul Hamilton, Brussels (BE); Stephen Harold Brown, Bernardsville, NJ (US); Yeo-Meng Lim, Singapore (SG)

(73) Assignee: ExxonMobil Chemical Patents Inc., Houston, TX (US)

(*) Notice: Subject to any disclaimer, the term of this patent is extended or adjusted under 35 U.S.C. 154(b) by 308 days.

(21) Appl. No.: 12/518,023

(22) Filed: Jun. 5, 2009

(65) Prior Publication Data

US 2011/0124827 A1 May 26, 2011

Related U.S. Application Data

(63) Continuation of application No. PCT/EP2007/011289, filed on Dec. 20, 2007.

(30) Foreign Application Priority Data

Dec. 21, 2006 (GB) .................................. 0625528.5

(51) Int. Cl.
*C07C 2/00* (2006.01)
*C07C 2/02* (2006.01)
(52) U.S. Cl. ..................... 585/501; 585/502; 585/520
(58) Field of Classification Search .................. None
See application file for complete search history.

(56) References Cited

U.S. PATENT DOCUMENTS

| | | | | |
|---|---|---|---|---|
| 2,440,822 A | * | 5/1948 | Hachmuth | 585/300 |
| 2,694,002 A | | 11/1954 | Hays | |
| 3,449,464 A | * | 6/1969 | Weber et al. | 585/516 |
| 4,487,985 A | | 12/1984 | Tabak | |
| 4,788,366 A | | 11/1988 | Harandi et al. | |
| 4,973,790 A | * | 11/1990 | Beech et al. | 585/533 |
| 5,650,475 A | * | 7/1997 | Marutani et al. | 528/26 |
| 5,672,800 A | | 9/1997 | Mathys et al. | |
| 6,684,914 B2 | | 2/2004 | Gershman et al. | |
| 2006/0199987 A1 | * | 9/2006 | Kuechler et al. | 585/502 |

FOREIGN PATENT DOCUMENTS

| | | |
|---|---|---|
| WO | WO 2004/005431 | 1/2004 |
| WO | WO 2004/005433 | 1/2004 |
| WO | WO 2004/009518 | 1/2004 |
| WO | WO 2005/113718 | 12/2005 |
| WO | WO 2006/133967 | 12/2006 |
| WO | WO 2007/006398 | 1/2007 |

OTHER PUBLICATIONS

Chitnis, G.K. et al., "ExxonMobil Olefins to Gasoline: EMOGAS™ Technology for Polymerization Units," National Petrochemical & Refiners Association (NPRA) Annual Meeting, Mar. 13-15, 2005, San Francisco, California.

* cited by examiner

*Primary Examiner* — David W Wu
*Assistant Examiner* — Elizabeth Eng
(74) *Attorney, Agent, or Firm* — Andrew B. Griffis; Leandro Arechederra

(57) ABSTRACT

In the oligomerization of olefins in a tubular reactor employing a molecular sieve catalyst, the temperature of the reaction is monitored and the space velocity of the olefin feed to the reactor is reduced as the temperature increases. This has been found to increase catalyst life and lead to extended production runs. Further extensions of the production run are achieved by improving reactor operating stability as the end of the production run approaches.

12 Claims, 1 Drawing Sheet

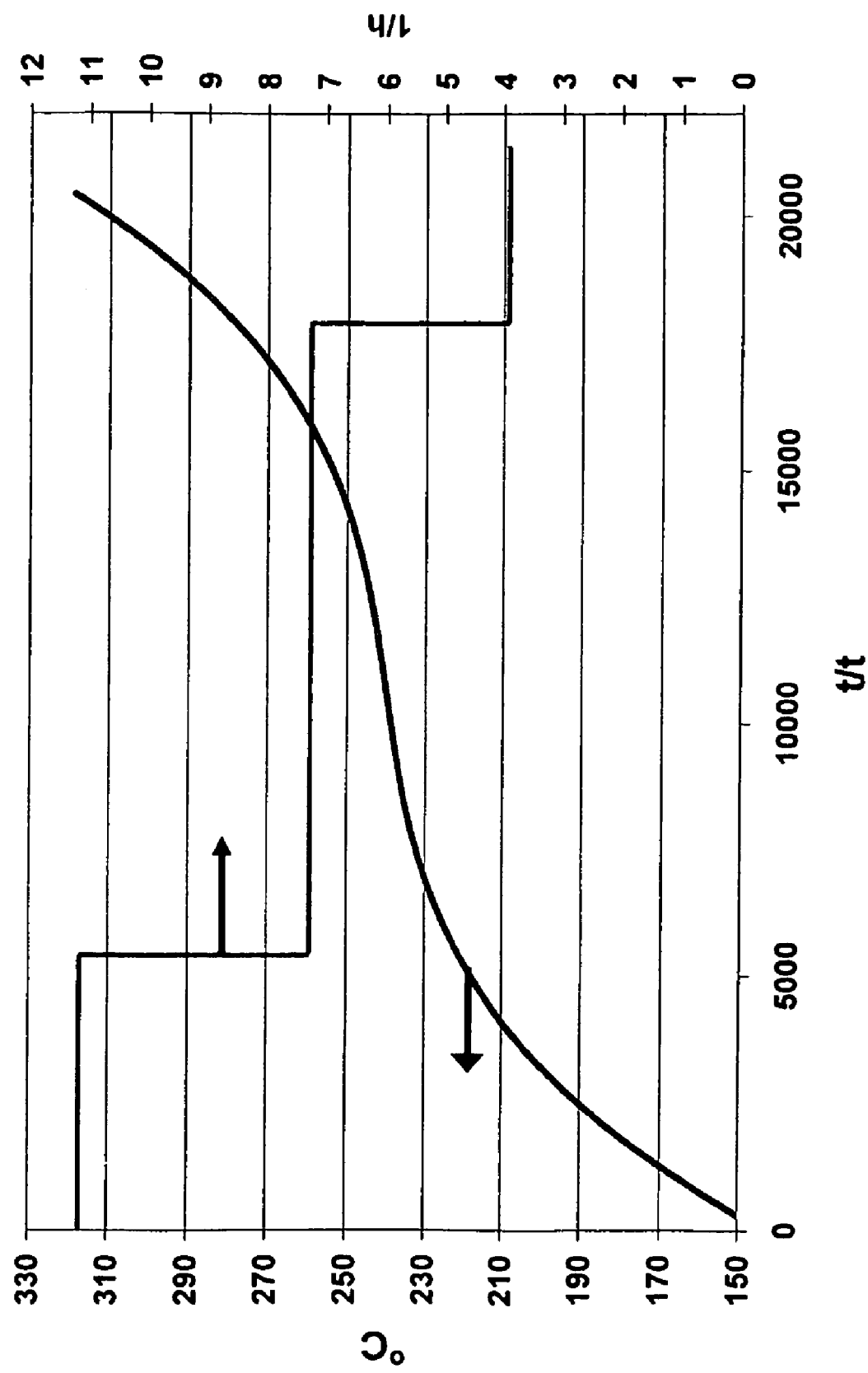

OLIGOMERISATION OF OLEFINS

CROSS-REFERENCE TO RELATED APPLICATIONS

This application is a continuation of International Application No. PCT/EP2007/011289 filed Dec. 20, 2007, which claims the benefit of Great Britain Patent Application No. 0625528.5 filed Dec. 21, 2006, the disclosure of which is fully incorporated herein by reference.

FIELD OF THE INVENTION

The present invention relates to improvements in or relating to the oligomerisation of olefins over a molecular sieve or zeolite catalyst in tubular reactors. On an industrial scale it is desirable that oligomerisation reactors can run continuously for as long as possible (i.e. long catalyst life) and that the conversion and selectivity of the reaction is maintained over such extended production runs.

BACKGROUND OF THE INVENTION

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as propene, 2-methylpropene, 1-butene and 2-butenes, pentenes and hexenes) can be converted by oligomerisation to a product which is comprised of oligomers and which is of value as a high-octane gasoline blending stock and as a starting material for the production of chemical intermediates and end-products. Such chemical intermediates and end-products include alcohols, acids, detergents and esters such as plasticiser esters and synthetic lubricants. Industrial oligomerisation reactions are generally performed in a plurality of tubular or chamber reactors. Solid phosphoric acid, ion exchange resins, liquid phosphoric acid, sulphuric acid, molecular sieves, and zeolites, are known catalysts for oligomerisation.

Industrial hydrocarbon conversion processes employing zeolite catalysts typically run for several weeks or months before a catalyst change is required or a decommissioning of the reactor is needed. There is a general desire to increase run length to increase catalyst use and to reduce the amount of down time. However it is necessary to balance increasing the run length with the production of the desired product. Various attempts have been made to accomplish this, such as by the development of new catalysts or the control of temperature and pressure in the reactors as is described in PCT patent application PCT/EP2006/005851.

There are therefore continuing attempts to increase run lengths and these have led to olefin oligomerisation runs of several months. In industrial processes the feeds for the reactions are generally streams derived from catalytic or steam cracking, which may have been subjected to fractionation and other cleanup treatments. The nature of such refining activities is such that there will be variations in the composition of the feed. In addition, it may be desired to change the nature of the feed during a reactor run. The optimum catalyst activity and the optimum reaction conditions vary according to the composition of the feed. Furthermore, the reactions are exothermic and the exotherm also depends upon the nature and amount of olefin present in the feed. Butylenes, but especially isobutylene and propylene are particularly reactive feedstocks generating a large exotherm.

The feeds that are used for olefin oligomerisation are typically obtained from petroleum refining or petrochemical operations. In particular they are obtained from either the steam cracking or catalytic cracking of streams obtained from the processing of crude oil. The compositions of these oligomerisation feeds depends upon the feed to the cracking process and the cracking conditions that are employed. The composition of the oligomerisation feed and particularly the amount and nature of the impurities in the feed can have a significant impact on the conversion and selectivity of the oligomerisation reaction and can also effect the useful lifetime of the catalyst. Recently steamcrackers have been developed to process whole crude oils or the heavy fractions from crude oil distillations. Such feedstocks contain particularly high levels of nitrogen or sulphur. Examples of steamcracking process suitable for such feedstocks are described in WO 2005/113718 A2, WO 2004/005433 and WO 2004/005431, which are incorporated by reference. Alternatively the feeds may be produced by the conversion of oxygenates such as methanol to olefins.

It is well known that certain impurities such as sulphur containing contaminants and basic nitrogen containing species, including those compounds that are Lewis base, have an adverse effect on the useful lifetime of the catalyst and processes are employed to remove these contaminants from the feeds.

The present invention is concerned with oligomerisation processes that employ a zeolite oligomerisation catalyst in a tubular reactor and is particularly concerned with the provision of conditions which enhance the overall conversion and selectivity of the reaction and extend catalyst life. The present invention is concerned with reactions performed in tubular reactors, and although in no way limited to such the invention, is concerned with the production of octenes by the dimerisation of butene streams.

Octenes are used as feedstocks for hydroformylation for the production of $C_9$ aldehydes, and upon hydrogenation of $C_9$ alcohols, which are useful chemical intermediates such as raw materials for the production of plasticiser esters such as dinonyl phthalate. The plasticiser performance is dependent on the structure of the nonyl group which in turn is dependent upon the structure of the octene molecule from which the nonyl alcohol is produced. Octenes produced by the oligomerisation of olefines such as butene or butenes, including isobutene, tend to be a mixture of isomers of octene. Typically the isomers contain 1, 2 or 3 branches along the molecular backbone. The octenes are categorised by the average degree of branching, which is determined by first hydrogenating the mixture of isomers to remove unsaturation and then analysing the product of hydrogenation by gas chromatography for their individual isomers. The lower the degree of branching of the octene, the lower the viscosity of the plasticiser esters derived from the nonyl alcohol obtained from the octene, and the more effective the plasticiser. The invention is therefore concerned with improving the conversion and selectivity of a continuous olefin oligomerisation process, and in particularly to extending the period of time over which the improved conversion and selectivity can be achieved. In a preferred embodiment, the invention is concerned with improving the conversion and selectivity of a continuous process for the production of octenes by the dimerisation of butene. On butenes feed, the term overall selectivity relates to the ability to produce octenes, and the term structural selectivity relates to the ability to produce desirable octene isomers within the overall octene production.

Throughout this application, conversion is the percentage of fresh olefin feed that has reacted (and hence not retrieved anymore in the stream(s) leaving the process). It may be determined by making a material balance over the reactor/process and calculating % conversion of olefin as 100×(In−Out)/In.

Overall selectivity is typically defined as the production of the selected desired product(s). On (primarily) $C_4$ feed these are typically the octene molecules, although the dodecenes may be included, and on (primarily) $C_3$ feed these are the hexenes and dodecenes but even more importantly the nonene molecules. On mixed $C_4/C_5$ feeds these are the octenes and nonenes (and optionally the decenes), and on mixed $C_3/C_4$ feeds these are the hexenes, heptenes, octenes, nonenes (and optionally the decenes). Undesired typically are the heavier oligomers (typically the $C_{10}$ or $C_{11+}$ molecules, except for the tetramer (mainly $C_{12}$) that is made from propylene), and the molecules that are not directly made by oligomerisation of fresh feed olefins, but made via a mechanism involving cracking to other than those fresh feed olefins. On $C_4$ feeds those are typically everything but the octenes. On $C_3$ feed, it are those other than $C_6/_9/_{12}$s. Selectivity is expressed as a % wt found of the desired material relative to the amount of reaction products (excluding unreacted olefins and paraffins).

Structural selectivity is defined as the production of desired isomers within a mixture of isomers of a particular compound. This is determined by hydrogenation of the olefin to remove unsaturation which can interfere with a gas chromatogram and analysis of the product by gas chromatography. It is then possible to determine the number of molecules with 0, 1, 2 and 3 branches and from this the branching index may be calculated as the average number of branches per molecule. It is known that the structural selectivity and selectivity in the production of octenes from butene feeds can be improved by employing a process involving a relatively low conversion per pass combined with high recycle for high overall conversion, and this may be combined with increased reaction temperature. This technique is said to result in improved structural selectivity and a high overall conversion and selectivity to the preferred octene oligomer.

Throughout an extended oligomerisation production run, as the catalyst activity reduces, the reaction temperature is generally increased to maintain the desired level of conversion, and the reaction is terminated when a certain temperature representing the limits of the apparatus is reached for the desired level of conversion. Catalyst life or reactor run length is typically expressed as the amount (i.e. weight) of oligomer made per amount (weight) of catalyst, usually as ton/ton, lb/lb or kg/kg, and this provides a value that compensates for throughput variations, and this is a result of the material balance over the process throughout the run. The highest temperature that can be tolerated depends upon the equipment and the feed employed although we prefer to terminate with a temperature in the steam drum, in case one is provided, at less than 300° C., more preferably at less than 270° C. to avoid oligomer cracking reactions. This may allow the maximum temperature in the reactor tube or tubes to be as high as 310° C. or even 325° C., depending on the tube and reactor design.

Tubular oligomerisation reactors employing zeolite catalysts typically comprise one or more bundles of tubes also termed "reactor tubes", mounted, preferably vertically, within a shell. The tubes are packed with the zeolite catalyst, typically in the form of pellets, and the feed containing olefin reactant is passed through the tubes in which it is oligomerised, typically from top to bottom. The length of the tube in industrial practice is generally from 2 to 15 meters, often from 3 to 14 meters, preferably from 5 to 12 meters, more preferably from 6 to 11 meters, yet more preferably from 8 to 10 meters. The diameter of the tube, the thickness of the walls of the tubes and the materials from which the tubes are made are important, since oligomerisation reactions are exothermic and it is important to dissipate the heat generated by the oligomerisation reaction. Accordingly, relatively small diameter, such as an external or outer diameter (OD) from 25 to 75 mm, tubes are preferred, more preferably 35 to 50 mm diameter (OD) tubes. The reactor tubes are preferably of high strength material and are thin walled and of a material with a high thermal conductivity. The high strength is required to withstand the high pressures that are generally used in the oligomerisation of olefins in a tubular reactor employing a zeolite catalyst. Duplex stainless steel is a preferred material for manufacture of the tubes. Higher strength steel and smaller tube diameters allow for smaller wall thicknesses. Duplex stainless steel and a 50.8 mm (2 inch) OD tube allow the wall thickness to be as little as 3 to 4 mm, leaving an internal diameter of the tube of 35-45 mm.

Any convenient number of tubes may be employed in a tubular reactor shell. Typically, operators use from 25 to 500 tubes per shell, arrayed in parallel. Preferred reactors contain about 77 tubes or 180 tubes per shell, although any number may be employed to suit the needs of the operator, e.g. 360 or 420. The tubes are preferably mounted within the shell and a temperature control fluid is provided around the outside of the tubes but within the shell to dissipate heat generated by the exothermic reaction that, in use, takes place within the reactor tubes. One reactor may comprise multiple bundles of tubes, for example up to 7 or 8, or even 9 bundles, and preferably, in use; the temperature of the fluid within the tubes in all the bundles in the same reactor is controlled by means of the same temperature control fluid system. Hot oil or boiling water, under pressure to control the temperature, may be used as the temperature control fluid. Reference to the temperature of tubular reactors as a whole herein is a reference to the temperature of the temperature control fluid, other discussions relate to temperature profiles within individual tubes.

Historically, oligomerisation reactions over acid catalysts are performed in the presence of water. The light olefinic feedstreams from refinery operations that are used for olefin oligomerisation typically contain water vapour from upstream in the process, because it is either added such as in steamcracking or catalytic cracking, or formed such as in the process of converting oxygenates to olefins. The feedstreams are therefore typically at their water dew point when they are condensed. This water will typically condense together with the light hydrocarbons, and there is usually sufficient water present to form free water that is then separated off by gravity. The liquid hydrocarbon stream containing the olefinic feed for oligomerisation is immiscible with water and has a lower density. It will tend to form a separate liquid layer above any liquid water phase. Due to some degree of water solubility, this layer will contain dissolved water. If a free water phase is formed, the level of dissolved water will be up to the solubility limit of water in the hydrocarbon stream. This limit is different for different hydrocarbon components, and therefore depends on the composition of the hydrocarbon stream.

U.S. Pat. No. 5,672,800 (WO93/16020) is concerned with the oligomerisation of olefins employing a zeolite catalyst, particularly the zeolite ZSM-22. U.S. Pat. No. 5,672,800 does not indicate the nature of the reactor that was used although it employs small quantities of materials and indicates that under the conditions employed in U.S. Pat. No. 5,672,800 conversion and catalyst life can be improved if the oligomerisation is performed in the presence of water. The compositions in the examples show a significant improvement in catalyst life when water is present. The catalyst life achieved on propylene using the techniques of U.S. Pat. No. 5,672,800 is 1240 weight of oligomer per unit weight of catalyst and 2500 weight of feed per unit weight of catalyst. According to U.S. Pat. No. 5,672,800, if the feed has a water content of from 0.05 to 0.25% molar, preferably at least 0.06% molar, based on the hydrocarbon content of the feedstock, the yields of the desired higher molecular alkene oligomers can be increased and the zeolite catalyst becomes deactivated more slowly. U.S. Pat. No. 5,672,800 specifies that if the water content is below 0.05 molar %, it should be increased. In Example 1 of U.S. Pat. No. 5,672,800 the moisture content of a feed having an initial water content of 0.02 molar % is hydrated to give a water content of 0.15 molar %, and the catalyst life is increased significantly, as is the propene conversion. U.S. Pat. No. 6684914 also hydrates the olefin feed to at least 0.05 mole % water. International Publication Number WO 2004/009518 suggests that the minimum water content of the hydrated olefin feed should be 0.005 wt %.

Although the use of water had been found to be beneficial, the water can interact with the zeolite to form oxygenates from the hydrocarbons in the feed. Although the reaction is not fully understood, it is believed that some of the olefins in the feed and the water react over the catalyst to form alcohols and ketones, which can be converted to acids, which have been found to cause severe corrosion downstream, particularly in the overhead of the first distillation tower, typically called the stabiliser column, and associated equipment for recycling unreacted feed molecules. This corrosion possibility requires equipment replacement and associated down time and/or the selection of more expensive corrosion resistant construction materials. PCT patent application PCT/EP2006/005852 relates to an oligomerisation process in which the olefin-containing feed stream contains less than 30 ppm wt of water.

The ExxonMobil Olefins to Gasoline (EMOGAS) process was described at the Annual Meeting of the National Petrochemical and Refiners Association, 13 to 15 Mar. 2005, at the Hilton Hotel, San Francisco, Calif., USA. The paper described olefin oligomerisation in a tubular reactor employing a zeolite catalyst, and specified that the reaction temperature is controlled with water that is fed on the shell side of the reactor. It is stated that the heat released due to EMOGAS reactions in the tubes evaporates water on the shell side. The temperature profile in the tubular reactor is said to be close to isothermal and the temperature is controlled via the shell side water pressure, which controls the temperature of evaporation, and also by the reactor feed temperature. The tubular reactors are said to usually operate at a pressure between 5.5 and 7.6 MPa (800 and 1100 psi) and at temperatures around 204° C. (400° F.).

The EMOGAS brochure also shows chamber-type reactors using interbed quench for temperature control. Adiabatic reactors in series for oligomerisation using interbed/interreactor cooling for temperature control are discussed in U.S. Pat. Nos. 4,487,985 or 4,788,366.

Reference in this specification to removal of heat from the (reactor) tubes of tubular reactors or temperature control of the (reactor) tubes is, in context, intended to mean removal of heat from the materials contained within the tubes where reaction takes place (generally comprising, in use, unreacted feed, reaction products and catalyst). It will be appreciated that the heat generation on the catalyst and heat removal from the tube wall may cause a radial temperature gradient through the cross-section of the tube, such that the centre of the tube may become significantly hotter than the wall of the tube. The larger the tube diameter, the larger this temperature gradient may be. One convenient way to remove the heat from the tubes and carry out the temperature control is to provide boiling water to generate steam within the reactor, on the shell side around the exterior of the tubes. This provides a good heat transfer coefficient on the shell side. If the present invention is performed in a chemical plant or a refinery, the steam generated by the oligomerisation process may be readily integrated into the steam system typically present at such sites. The reaction heat from oligomerisation may then be put to use in another part of the oligomerisation process, or with another process in the plant or the refinery, where heat input is required.

As already indicated, the oligomerisation of olefins over a zeolite catalyst is a highly exothermic reaction, particularly the oligomerisation of propylene and/or butylenes such as isobutylene. The high temperatures generated by the exotherm can lead to carbonaceous deposits on the catalyst caused by a build up of condensed, heavy hydrocarbons similar to asphalt. Such deposits are commonly termed "coke", and may occur inside the zeolite pores and/or on the outer surface of the catalyst. This coke formation can lead to deactivation of the zeolite catalyst. In general, the higher the concentration of olefin in the feed, the higher will be the rate of heat release from the catalysed reaction, and hence the higher the temperatures that can be reached on and/or in the catalyst. Consequently there will be a higher rate of coke formation. This has placed a limit on the maximum concentration of olefin that can be tolerated in the feed. Since the oligomerisation reaction is highly exothermic, it is necessary to control the temperature and in a tubular reactor this is usually accomplished by encompassing a bundle of reactor tubes within a shell through which is passed a temperature control fluid. Conveniently, the temperature control fluid is oil (usually hot oil), or preferentially a boiling liquid because of the improved heat transfer this brings on the side of the boiling liquid. This boiling liquid may be an organic stream, preferentially a stream taken from another point in the process and its return stream, usually a mix of vapour and liquid, may be returned to another suitable point in the process. The reaction heat may as such be used as heat supply to a reboiler of a distillation tower. Most conveniently, the liquid is water, at least partially converting to steam in the reactor shell side. The water is conveniently supplied from a steam drum and the boiling temperature can then readily be controlled by varying the pressure in the steam drum. Conveniently, the steam drum collects the water/steam return stream from the reactor shell side, and provides the water supplied to the reactor shell side, most conveniently by thermosyphon action, avoiding the need for pumping or other means to drive the circulation. The steam generated by the reaction heat may be removed from the steam drum and may be put to use elsewhere. The temperature of the generated steam, or in such case of the temperature control fluid, exiting the reactor, is considered the temperature of the reaction, because it is the single most representative temperature for the reaction throughout the reactor.

When the conversion obtained in the reactor reduces, due to catalyst aging and/or coking, the reactor temperature is typically increased to compensate for the reduced catalyst activity. This is conventionally done by raising the steam pressure on the shell side of the reactor, which increases the temperature at which the heat exchange fluid boils. This procedure is called temperature ramping, and is typically limited up to a maximum temperature, when the reactor is typically taken out of service. Such temperature ramping is for instance disclosed in US 2006/199987, wherein a relatively constant olefin conversion is thereby ensured at a given weight hourly space velocity (WHSV).

U.S. Pat. No. 2,694,002 (Georges E. Hays) discloses a process for the polymerization of olefins in a first polymerization zone in the presence of a catalyst composed of oxides of silicon and aluminum in controlled ratio, the effluent thereof further threated in a second polymerization zone in the presence of a solid phosphoric acid type catalyst. In each zone, temperature, pressure and space velocity may be regulated, so that within a desired total conversion, the selectivity disadvantages of the two different catalyst systems are avoided and an improved selectivity to the desired gasoline components is achieved. U.S. Pat. No. 2,694,002 is not concerned with extending reactor runlength or catalyst life.

U.S. Pat. No. 2,440,822 (Karl H. Hachmuth) discloses a process for conducting catalytic reactions in heterogeneous catalyst portions used in parallel and that differ in activity. The process is described in more detail in connection with the polymerization of normally gaseous olefins to gasoline-range hydrocarbons, without specifying what type of catalyst should be used. The process of U.S. Pat. No. 2,440,822 controls the feed temperature to each of the adiabatic reactors in order to obtain the reaction zone temperature that is necessary in each of the reactors for achieving the desired conversion, which may be different and depend on the volume, the type and/or the age of the catalyst in the reactor. Further improved results may be obtained in the process of U.S. Pat. No. 2,440,822 by lowering the rate of flow to a relatively less active or relatively deactivated catalyst portion, because the lower flow rate decreases the average reaction zone temperature required in such a reactor and thereby decreases the rate of deactivation of the catalyst therein.

We have now found that the run life can be further extended by appropriate control of the space velocity of the olefin containing stream that is fed to the reactor. The space velocity is defined as the rate of feed supplied per hour divided by the weight of catalyst in the reactor.

SUMMARY OF THE INVENTION

Accordingly, the present invention provides a continuous process for the oligomerisation of olefins employing a molecular sieve or a zeolite catalyst wherein an olefin containing hydrocarbon feed is passed over a bed of the molecular sieve or the zeolite catalyst in a tubular reactor wherein the shell side of the reactor is cooled by a temperature control fluid and the temperature of the reaction is monitored and the space velocity of the olefin stream fed to the reactor is adjusted according to the temperature measured.

By this process, within a desired average reaction temperature required for a target conversion, the axial temperature profile in the reactor tube is flattened in the early part of the run, and is again sharpened in the last part of the run, both effects contributing to a more gradual catalyst deactivation and a longer overall catalyst life.

BRIEF DESCRIPTION OF THE DRAWINGS

FIG. 1 illustrates how the space velocity of an olefin stream fed to an oligomerisation reactor may be adjusted throughout the reactor run and according to the (average) reaction temperature measured.

DETAILED DESCRIPTION

At the beginning of a run, when the catalyst is fresh or freshly regenerated and is having a high activity, the temperature profile along the reactor tube is typically showing a sharp peak, with the peak temperature occurring close to the inlet of the reactor. We have found that it is beneficial to operate at the start of run with a relatively high space velocity, i.e. with a space velocity that is above the average over the entire run, because, for the same average reaction temperature, the temperature profile is flatter and the peak temperature is lowered relative to the (average) temperature of the reaction. This reduces the catalyst deactivation rate around the location of the peak temperature and thereby contributes to a longer reactor runlength.

During an extended production run (particularly on feeds containing little or no undesired impurities these are lasting several months or more) the reaction temperature will gradually increase over the initial phase of the reaction and will then reach a period of substantially stable conditions which are considered to be the optimum conditions according to the nature of the feed employed and the catalyst used. These conditions are then maintained until the catalyst deactivates and the temperature is increased again. We have found that the use of these conditions may be prolonged if the space velocity of the feed is reduced once the optimum conditions are reached, i.e. if the reactor is operated at a space velocity that is about the average over the entire run.

Despite the prolongation of the optimum conditions, eventually the temperature will start to increase again and we have found that the run length can be further prolonged if the space velocity of the feed is further decreased. i.e. if the reactor is operated at a space velocity that is below the average over the entire run. By lowering the space velocity, the reaction is concentrating in the zone around the peak temperature. Thereby the relatively flat temperature occurring closer to the end-of-run is sharpened and the peak temperature is increased relative to the average reaction temperature. This reduces the need for a higher feed temperature, reduces vulnerability to fluctuations such as feed temperature or olefin concentration drops that may extinguish the reaction. It also reduced catalyst deactivation downstream of the peak temperature. With the sharpened temperature profile, the peak temperature can move further down the reaction tube before the desired conversion cannot be reached anymore within the limitation of a maximum average reaction temperature, or as the case may be, steam drum temperature and/or pressure.

The actual velocities that should be used in the various phases of the run depend upon the nature of the feed, the nature of the catalyst used, and the nature of the product it is desired to produce. In the preferred embodiment, which involves the production of octenes from butenes, the conversion per pass and the degree of recycle required for the overall conversion of the feed are established, and the conditions throughout the run can then be varied according to the present invention in order to ensure an extended production run, yielding a product having the desired branchiness.

The present invention is particularly useful when employed together with the techniques described in PCT patent application PCT/EP2006/005851 and in PCT patent application PCT/EP2006/005852 which relate to instantaneous temperature control of the reactor and to the reduction of the water content of the olefin feed to improve catalyst life. In particular the reduction in the water level has been found to improve the life of the catalyst with feeds containing nitriles such as acetonitrile or propionitrile. We have further found that catalyst life is further extended if the level of nitriles, or other organic nitrogen containing Lewis base, in the feed is below 5 ppm by weight in combination with a level of water in the feed below 30 ppm by weight. Patent applications U.S. Ser. No. 60/781,623 and PCT/EP2006/005852 relate particularly to this subject.

Accordingly, in a preferred embodiment the present invention is applied to a hydrocarbon olefin containing stream containing less than 30 ppm of water and less than 5 ppm of an organic nitrogen containing Lewis base, based on the weight of hydrocarbon in the feed.

In particular, the feed contains less than 5 ppm acetonitrile and/or propionitrile. Preferably the level of nitriles in the feed is below 3 ppm, more preferably below 2 ppm, even more preferably below 1 ppm by weight.

The present invention is particularly useful when applied to the oligomerisation process described in copending Patent Application PCT/EP2006/005851 or its priority application GB0512377.3.

We have found that the techniques of the present invention can reduce the temperature fluctuations along the length of a reactor tube, and improve the control of the temperature along the length of the reactor tube, in order to enhance the life of the catalyst and the conversion achieved. The maximum temperature of the temperature ramping may be imposed by the design pressure and/or temperature of the reactor itself, the reactor shell side, or, if present, the steam drum. The maximum temperature may also be determined by undesired side reactions becoming too prominent above a certain reactor temperature. When that maximum temperature is reached and catalyst activity reduces further, feed flow rate may be reduced in order to maintain olefin conversion.

We have found that as or after the reactor run has reached about 75% of its total length and feed flow rate is reduced, its operations typically start to face a problem of operating stability, due to the changes in its enthalpy balance. The problem and its possible solutions are here discussed for a reactor shell side cooled by a steam generating system, typically thermosyphon driven, but it applies mutatis mutandis to other embodiments of tubular reactors. On one hand, the heat generated in the reactor continues to reduce, due to declining catalyst activity. On the other hand, most of the heat consumptions and losses continue to increase due to the increasing reactor operating temperature. The net steam production, which is a result of the enthalpy surplus between enthalpy production and consumption plus losses, reduces significantly compared to earlier during the run. We have found that once this net steam production falls to zero, due to the enthalpy consumers and losses becoming larger than the generated reaction heat, the reactor operation cannot be further sustained, reactor temperature starts to drop in an accelerating fashion, and the reaction extinguishes. Because of the low catalyst activity at the later part of the run, the required temperature to get reaction started cannot be reached with the available external heating means, the reactor cannot be restarted anymore and the catalyst needs to be replaced. As the reactor approaches its end-of-run, small variations in the enthalpy balance can trigger such a downward spiral and hence a reactor shutdown.

We have now found that certain solutions can be implemented, all targeted to minimize the risk for such unplanned reactor shutdowns. They all minimize the vulnerability of the reactor operations to unintentional variations in the enthalpy balance, and therefore are able to achieve a significant extension of the reactor run length.

A first solution relates to the steam pressure control system. This control system, which is usually a control valve, is typically designed for the higher steam production rates and the low steam generating pressure of earlier in the run. The generated steam can only be directed to a low pressure outlet at that time, and the control system needs to be designed for that service. A minimum pressure drop over the control system to make it operable is typically 1 bar. At the end of run, the control system is operating in a regime that is suboptimal and vulnerable to variations, because it sees a relatively high available pressure drop, but has to control a volumetric steam flow that is relatively low. We have found that this vulnerability can be reduced by keeping the pressure drop over the steam pressure control system below a maximum value, such that the control system keeps its ability to control the upstream pressure under the end-of-run conditions. We prefer this maximum pressure drop to be at most 50 bar, preferably at most 30 bar, more preferably at most 20 bar and even more preferably at most 10 bar. This can be achieved by various means or a combination thereof. The preferred solution is to shift the steam outlet from the lower pressure outlet at the start of run to a higher pressure level outlet as the steam generation pressure has increased sufficiently to allow this shift. It brings the benefit that the steam can be put to use at a higher pressure, where it is of higher value. The higher this outlet pressure is, the more preferred this solution is because of the higher value of the steam. It is preferred to maintain at least 1 bar pressure drop over the control system. An alternative is to provide a valve, downstream of the pressure control system, that can be partially throttled, such that the pressure is reduced in two steps. Three or more pressure reduction steps could be applied, but this is less preferred. Another alternative is to provide a second control system in parallel to the main control system, the second system being designed for the duties closer to the end of the run. During the run, the steam pressure control may then be switched from the first control system to the second control system as the reactor run is approaching end-of-run conditions, such as at about 75 or 80% of its total run length. Yet another alternative is to provide a control system comprising a pressure control valve having an adjustable $C_v$, preferably a valve that is also designed for easy trim and/or seat replacement to change the valve characteristics over an even wider range. A suitable example is a MASONEILAN® Varipak control valve. In this alternative as the reactor run proceeds, and in particular when about 75% or 80% of the expected runlength has been reached, the valve characteristics (such as its $C_v$) are modified to improve the responsiveness of the valve to process changes. In addition or alternatively, the valve may be decommissioned for a period during which the controlled stream flows through the valve bypass, and the valve trim and/or its seat may be changed to a different size, preferably a smaller size, and the control valve may be recommissioned. This also enhances the valves responsiveness to process changes, and ultimately allows to reach longer reactor runlengths.

As an example, when a steam drum is operating at 40 barg and the steam is routed to a 10 barg main header, there is 30 bar pressure drop over the valve. If the steam outlet is switched to a 25 barg main header, the pressure drop over the valve becomes only 15 bar. For the same steam flow, this 50% reduction in pressure drop allows the control valve to operate at a much higher % opening, where its control capabilities are better and it is much better in reacting to process variations.

We have found that the operability of the reactor at the end of run can be further improved, and therefore the reactor run can be further extended. This is done by minimizing enthalpy consumptions and losses that are internal to the reactor system.

A first of such enthalpy consumptions is the enthalpy required to heat the mass of reacting fluid up from its feed temperature to the reactor outlet temperature. We have found that with parallel reactors, it is preferred to provide individual reactor feed preheaters, such that reactor feed temperatures can be individually controlled. The reactor feed temperature for a reactor is then preferably increased as it proceeds towards end-of-run, resulting in a higher net steam production, which makes the steam flow easier to control and less vulnerable to process variations. We prefer the reactor feed to be maintained at a temperature that is not more than 80° C. below the temperature of the control fluid exiting the reactor, or in this particular case the temperature of the steam leaving the steam drum. Preferably, the reactor feed is maintained at a temperature not more than 60° C., more preferably not more than 50° C., even more preferably not more than 40° C., yet more preferably not more than 30° C. and most preferably not more than 20° C. below the reference temperature, i.e. the temperature of the control fluid exiting the reactor. This feed temperature control relative to the reference temperature (and if applicable steam pressure) can readily be automated, preferably by on-line computer control.

The second of such enthalpy consumptions is the enthalpy required to heat the supply of temperature control fluid, which in this particular case is the boiler feed water supply to the steam drum, from its supply temperature to its boiling temperature. We have found that the reactor operation becomes more stable at the end of run if this supply fluid can be provided at a higher temperature, such that its contribution as a consumer on the enthalpy balance is reduced. With multiple reactors in parallel, this may be achieved by using a common preheater on this supply fluid. It is however preferred to have individual temperature control of each supply stream to each individual reactor, such that the effects can be maximized per reactor by adjusting the boiler feed water supply temperature when the steam drum pressure control is changed. Whatever the preheating means and the temperature control system, we prefer to have the supply of temperature control fluid to be maintained at a temperature that is not more than 80° C. below the reference temperature as defined above. Preferably the supply of temperature control fluid is maintained at a temperature that is not more than 60° C., more preferably not more than 50° C., even more preferably not more than 40° C., yet more preferably not more than 30° C. and most preferably not more than 20° C. below the reference temperature, i.e. the temperature of the control fluid exiting the reactor. Also these temperature controls (common and/or individual) can be readily automated, preferably by on-line computer control.

A third consumer on the enthalpy balance, typically associated with a vaporising temperature control fluid, is the purge of liquid fluid from the vaporising system, required for liquid composition control. In a steam generating system, this is the blow down of water from the steam drum required to keep the water quality acceptable, such as controlling the salt concentration below the level where precipitation may occur, and fouling of the heat exchange surfaces and other sensitive elements of the equipment. This purged fluid leaves the system at a higher temperature than it is supplied, and hence heat is consumed by the purge. In simple systems, the purge flow is typically kept constant. At the end of run, when the net vapor or steam production is less, we have found that the purge flow is preferably reduced, such that its enthalpy consumption effect is not larger than what is required for composition control. In one embodiment, the purge flow or blow down may be manually reduced stepwise through the reactor run, such that it is maintained in the range from about 1% to 5% of the supply flow of temperature control fluid. In a preferred embodiment, the purge stream is automatically controlled within this range of 1 to 5%, and even more preferably from 2 to 4% of the supply flow. It is understood that the purge requirements are lower as the incoming levels of impurities are lower, and/or as the system is able to tolerate higher levels of these impurities, such as when the impurities consist of salts that have a higher solubility. In a preferred embodiment, the purge flow is controlled by flow control, more preferably by flow ratio control, even more preferably automated and most preferably by on-line computer control.

We have found that by applying the proposed solutions to a tubular zeolite oligomerisation reactor, the reactor run length could be extended from 2000 ton/ton before the solutions were implemented, up to 2500 ton/ton when the following solutions were implemented: (i) steam outlet is changed from atmospheric venting at start of run, as soon as possible in the run switched to an outlet main at 9 barg and later to a main at 20 barg; (ii) the reactor feed temperature is controlled throughout the run such that it is not too cold, i.e. not more than 70° C. below the steam drum temperature; and (iii) the blow down flow from the steam drum is controlled throughout the run at or below 5% of the boiler feed water supply flow.

When this control possibility is exhausted, the reactor is considered to be at the end of its run and it is taken out of service, and the deactivated catalyst may be removed and regenerated. Regeneration may also be performed in situ. The catalyst may be replaced by fresh catalyst or by a different batch of regenerated catalyst.

In a preferred process for operating the present invention employing a tubular reactor, the desired per pass conversion and optionally the desired recycle amount is determined, and the reaction is started employing a high space velocity for the reactor feed of between 10 and 12 tons weight of feed per ton weight of catalyst per hour. The temperature of the reaction is monitored by measuring the temperature of the temperature control fluid or coolant, which is preferably continuously monitored, and typically there will be a steady increase day by day. After a certain period of time, and even more pronounced with pure feedstocks containing little to no catalyst poisons, it will however be observed that the temperature increase is declining towards a period of substantially stable conditions, i.e. practically a steady state. At this stage, it is preferred that the space velocity of the feed should be reduced to a medium value to prolong the run, and typically a space velocity of from 6 to 10 is appropriate. We have found that these conditions can be sustained at constant temperature for an extended period, which may be several months on the purer feeds. However, eventually an increase in the temperature will be observed, and we have found that the conversion per pass, and the production of a product with the desired degree of branching, can be sustained if the space velocity of the feed is then further reduced to a low value such as from 4 to 6. Eventually however, the temperature will increase to the level where it is necessary to decommission the reactor. We have however found that by employing the conditions of the present invention, reaction runs can be prolonged to over 10 months. We have also found that in a typical run for butene dimerisation using the Zeolite ZSM 57 as the catalyst, the initial phase involving temperature increase and high feed space velocity may have a duration of from 20 to 30%, typically about 25% of the total run time, the mid (the period of substantially stable conditions) (medium space velocity) phase may have a duration of from 40-60%, typically about 50% of the total run time and the final (low space velocity) phase the final 20 to 30%, typically about 25% of the run.

As mentioned, we prefer to use a dry feed when employing the present invention. The water content of the feed stream is preferably monitored continuously, more preferably employing an on line analyser. We have found that the water content may be determined by GC, we have also found that a Panametrics on line analyser, which employs a platinum on aluminium electrochemical probe, is particularly useful. The nitrile and other organic nitrogen containing Lewis base content of the feed is conveniently measured by on line gas chromatography, performed on the feed to the reactor. We prefer that the feed contains less than 30 ppm water by weight. If the water content of the feed exceeds 30 ppm then the feed can be dried by any conventional means. In processing of $C_4$ feeds, the feed to the reactor may be the $C_4$ byproduct derived from the production of methyl or ethyl tertiary butyl ether (MTBE or ETBE), which removes most of the isobutylene from $C_4$ refinery products by the formation of MTBE or ETBE. In the case of MTBE, this $C_4$ byproduct can contain dimethyl ether which needs to be removed by distillation, and this distillation step can, by appropriate tuning of the distillation conditions, also be used to remove any water in the $C_4$ byproduct stream that is the feed to oligomerisation down to the desired levels of 20 ppm or lower, preferably to 5 ppm or lower, and more preferably to 2 or even 1 ppm by weight or lower. The same may be applied in the context of ETBE production. Other examples of suitable drying techniques include fractionation, vapour stripping, liquid/liquid extraction using a hydrophylic fluid such as a glycol, and adsorption on a solid such as an adsorbent.

Removal of nitriles, or other organic bases, from the oligomerisation feed may be performed by a washing step with water, which should be performed upstream of the drying step. Alternatively, nitriles may be removed by adsorption on a selective adsorbent. An activated alumina (aluminium oxide), such as Selexsorb CD-X, or an acidic ion exchange resin such as DOW M-31 that comprises sulphonic acid may for instance be used in cases when the adsorbent treatment is employed. Typically, the performance of such adsorbents is negatively affected by the presence of water, meaning that with such adsorbents, the nitrile removal step is preferably performed downstream of the drying step.

The composition of material in the reactor varies as the material flows through, usually down, the reactor and begins to react. The olefin will have a lower molecular weight at the beginning (inlet) of the reactor, where the process flow is predominantly unreacted light olefins, and it will become progressively heavier towards the reactor outlet as the light olefins are oligomerised to form higher molecular weight olefins. Excessive temperatures caused by the exotherm of the reaction cause the oligomers to react further, thereby to form heavies which can coke up the catalyst, which leads to deactivation.

In typical operation of the preferred tubular reactor for oligomerisation of olefin feed, with zeolite catalyst with a temperature control fluid on the shell side, a temperature profile will be observed over the length of a reactor tube. Conventionally, such operation is performed with the tubular reactor arranged such that the feed inlet is at the top and the reaction product outlet is at the bottom. The following description addresses such an arrangement, but it will be understood that the description applies equally to reactors not in top to bottom arrangement. Typically, the temperature profile initially increases at the inlet of the tube, when reaction heat is generated faster than it can be removed by the temperature control fluid around the tube. As the reactants convert further as they move along the tube and their concentration reduces, the reaction rate reduces and the rate of heat generation reduces. At the same time, the temperature in the tube increases, and the heat removal rate through the tube wall increases. The temperature profile then typically goes through a maximum, and then shows a decline further along (down) the tube towards the outlet. As the reaction temperature declines along the tube, also heat removal rate reduces, and the temperature profile may then flatten out before the end of the catalyst bed in the tubes is reached.

In the known tubular processes employing fresh zeolite catalyst, the temperature increase at the initial part (e.g. top) of the tube can be sharp, and the temperature profile can show a sharp peak. The fresh catalyst at the initial part (top) of the tube performs most of the reaction. Coke will build up where the temperature is at its highest, which will deactivate the catalyst in that part of the tube and will then reduce the reactivity due to the catalyst deactivation, and hence the rate of heat generation will reduce, and hence the slope of the temperature increase in that part of the temperature profile declines. The catalyst further along (down) the tube will then see a higher concentration of unreacted reactants, and the reaction rate—and hence heat generation rate—will increase in that part of the tube. In this way the peak in the temperature profile, known as "the peak temperature", will move along (down) the tube. In order to compensate for the reduced overall catalyst activity, heat removal is typically reduced by increasing the temperature of the temperature control fluid around the tube. The average temperature in the reactor and the temperature at the outlet of the tube or reactor will thereby be increased as the run progresses. In addition, the temperature of the feed delivered to the tube inlet may be adapted as well. Typically it may be increased to keep as much of the reaction as possible at as early (high) as possible a location in the catalyst bed inside the tube. Any peak in the temperature profile therefore may not only move along (down) the tube as a production run proceeds but it may also become less sharp and less pronounced.

The rate of heat generation increases with higher reactant concentration. The peak in the temperature profile in the tube is therefore sharper and more pronounced when the olefin concentration in the feed to the reactor is higher. The rate of heat generation is also higher with more reactive reactants, typically with the lighter olefins such as propylene and butenes such as isobutylene. The peak in the temperature profile is therefore also sharper and more pronounced when a higher portion of the available butenes is isobutylene, or when a higher proportion of the olefins fed to the reactor is propylene. In case dienes or acetylenes are present, these are even more reactive and will increase the rate of heat generation, in particular in the upstream part of the zeolite catalyst bed. The total heat of the reaction also depends on the product produced. The greater the degree of oligomerisation of any particular olefin, the higher the heat of reaction, because more monomer molecules will have combined to form the product.

We have found that the techniques of the present invention enable the peak temperature to be reduced and in some instances to be eliminated. This is particularly the situation when the techniques are employed together with the techniques described in our copending Patent Application PCT/EP2006/005851 or its priority application GB0512377.3. PCT/EP2006/005851 or its priority application GB0512377.3 is concerned with the control of temperature and pressure within the reactor tube to within certain limits, whereby extended production runs with high conversion of olefin to oligomer may be achieved, using the conventional zeolite oligomerisation catalysts with feeds containing higher levels of olefin. According to PCT patent applications PCT/EP2006/005851 and PCT/EP2006/005852, the extended runs may be achieved without the need for the presence of water. In this way the corrosion of the reactor and/or in other parts of the process, in particular the stabiliser overhead system, and recycle equipment can be reduced. We have found that by also employing the techniques of the present invention the production run may be further extended.

The present invention therefore further provides a continuous process for oligomerising an olefin comprising contacting the olefin with a zeolite catalyst in a reactor tube of a tubular reactor having a shell that contains a temperature control fluid for removing heat of reaction from the reactor tube, in which process the olefin containing hydrocarbon feed to the reactor contains at least 42 wt % of olefin and less than 30 ppm of water based on total hydrocarbon in the feed, wherein operating conditions are controlled such that the reaction product mixture exiting the reactor is at a pressure of at least 55 barg and wherein the shell side temperature control fluid parameters are controlled such that the peak temperature in the reactor tube is no more than 50° C. above the temperature of the temperature control fluid as said fluid exits the reactor, and wherein the reaction temperature is monitored and the space velocity of the feed is varied according to the reaction temperature.

In particular, we prefer that the peak temperature be controlled to be no more than 40° C., preferably no more than 30° C., particularly preferably no more than 20° C., and most preferably no more than 10° C. above the temperature of the temperature control fluid as the temperature control fluid exits the reactor.

As is described in PCT patent application PCT/EP2006/005851 the flatter the temperature profile along the length of the tube, the easier it is to employ conditions that enhance catalyst life, in particular early and in the middle of the reactor run. Furthermore, a flatter temperature profile may be obtained if the overall throughput of the feed is increased, and in particular we prefer to employ a throughput of from 1 to 12 w/w/h, preferably from 2 to 9 w/w/h, more preferably from 3 to 8 w/w/h, which has been found to improve the heat transfer on the inside of a tubular reactor. According to the present invention, this flatter temperature profile may be sustained and further improved if the space velocity is varied throughout the run. In addition, a low per pass conversion such as a conversion of from 50 to 75%, coupled with recycle of unreacted components from downstream fractionation to the reactor feed, further flattens the temperature profile.

Where several tubular reactors are employed, it is preferred to provide separate preheaters for each of the reactors, so that the feed temperature can be adjusted according to the temperature conditions within the specific reactor. The employment of one or more of these conditions, together with low water level and the adjustment of the space velocity of the feed according to the present invention, has been found to result in a significant improvement in catalyst life.

We have found that, providing those conditions are employed, feeds of single olefins and mixtures of olefins can be processed in tubular reactors employing a zeolite catalyst over extended runs, for example up to at least 300 days continuous operation, without undesirable loss of catalytic activity. We have found that catalyst life in excess of 1500 tonnes of oligomer per tonne of catalyst may be achieved and catalyst life as high as 10,000 tonnes of oligomer per tonne of catalyst, even as high as 18,000 tonnes or higher can be achieved.

The feed streams containing the feed olefins such as $C_3$ and $C_4$ olefins are generally streams derived from steam cracking or catalytic cracking and the composition of the stream will depend upon the raw material from which it is produced and the production technology employed.

The maximum concentration of olefin in the feed that can be processed, will depend upon the nature of the olefin or mixture of olefins that are to be oligomerised. However, we have found that propylene containing feeds that contain e.g. up to 65 wt % propylene, more typically up to 60 wt % propylene, most typically up to 55 wt % propylene can be employed. Similarly we have found that butene-containing feeds that contain e.g. up to 80 wt % butene, such as up to 70 wt % butene, typically up to 65 wt % butene, most typically up to 60 wt % butene can be processed. Similar amounts can be processed when mixed $C_3/C_4$ feeds are employed. The minimum amount of olefin in the feed, according to the invention, is preferably 42 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably 50 wt %, such as at least 55 wt %, and most preferably at least 60 wt %.

In the embodiment of the present invention where peak temperature is controlled for satisfactory performance of the oligomerisation of olefins, for example $C_3$ to $C_6$ olefins, over a zeolite catalyst, the peak temperature in a tubular reactor may be measured by inserting a multipoint thermocouple in at least one of the reactor tubes. Spider-shaped inserts may be used to keep the thermocouple in the centre of the tube. It is preferred that the thermocouple can detect the temperature at various locations along a significant portion of the length of the tube, preferably towards the inlet end of the tube. Desirably, temperature is measured over at least the first 50%, or possibly 75% of the length of the tube from the inlet end, and at a plurality of points. For example, it is preferred to make measurements at from 10 to 20 points, such as 15 points, in a tube that is 3 to 10 meters (approx 10 to 33 feet) in length. The parameters of the temperature control fluid contained within the tubular reactor, for example the temperature and/or the flow rate, may then be adjusted in response to the temperature measured by the thermocouples, in order to maintain the peak temperature in the tube within the desired range according to the temperature control fluid outlet temperature. By appropriate adjustment of the parameters, this enables the process fluid temperature to be maintained at optimum conditions. Where the reactor consists of a number of parallel tubes, a multitude of those tubes may be provided with a multipoint thermocouple, although this is not essential.

The temperature of a tubular reactor is controlled by passing a temperature control fluid around the shell side of the reactor tubes. In a preferred embodiment, the tubular reactor consists of several tubes mounted vertically and in parallel and they may be mounted as a bundle or bundles of tubes. It is preferred that the olefin feed be introduced at the top of the tubes such that it passes through the tubes in a downward direction. The tubes are contained within a reactor shell, and the temperature control fluid preferably flows vertically upwards within the reactor shell in counter current to the direction of the flow of the olefin feed. Preferably, there are baffles provided on the shell side in order to guide the flow of the temperature control fluid. These baffles typically are arranged perpendicular to the reactor tubes. Alternatively arrangements may comprise co-current upflow or co-current downflow. In one embodiment of the invention, the temperature control fluid may be an organic fluid such as hot oil. However, in a preferred embodiment the temperature control fluid is water, preferably maintained at pressure in the range of 3 or 5 to 85 bar gauge, which results in a boiling temperature in the range of 150 or 160 to 300° C. The temperature of the water may be controlled by varying the pressure in the steam drum that separates steam from the boiling water, provides the water for boil up on the shell side of the reactor and collects the shell side outlet stream. In this way the peak temperature, wherever it may occur inside the reactor tube, may be controlled to be within the desired difference from the temperature of the temperature control fluid at the reactor outlet. The lowest reactor temperature, which is typically the inlet temperature, is preferably maintained at or above 140° C. In preferred operations the lowest temperature in the reactor tube is kept at least at 170° C., preferably at least at 180° C., more preferably at least at 190° C.

The improvements of the present invention are derived from the variation of the space velocity of the feed, and optionally in combination with the use of feeds containing less than 30 ppm water, and in a preferred embodiment from effective control of the temperature profile along the tubular reactor. We have also found that by employing feed delivery conditions with tubular reactors, e.g. an inlet pressure that establishes a minimum reactor outlet pressure of 55 barg, the reaction is improved. It is believed that these pressure conditions maintain the material in the reactor tubes of the tubular reactor in a single phase, which maybe a liquid phase or a dense phase. Accordingly, in a preferment of the present invention leading to further prolongation of the runs, the feed material is fed to the reactor under a pressure such that the material exiting from the outlet of the tubular reactor is maintained at a pressure of at least 55 barg, and thereby the inlet pressure will also be greater than 55 barg. Preferably the outlet pressure is in the range 60 to 80 barg and more preferably at least 65 or 70 or 75 barg. Provided the equipment can stand these operating conditions, a significant vapour phase and/or a two phase system, such as a vapour/liquid phase system, should preferably be avoided and particularly preferably avoided along the entire length of the tube.

In yet another embodiment, a plurality of oligomerisation reactors are placed in parallel. When the catalysts in the different reactors are not of the same age, this offers the opportunity to adapt the distribution of the total feed over the different reactors to optimize productivity in terms of conversion, temperature control and reactor run length. This balancing of feed over a set of parallel reactors may be assisted with on-line analyses of the reactor effluents, showing individual reactor conversions, and may be performed automatically by a multi-tiered control algorithm involving time delay calculations to keep the overall process as close as possible to its optimum productivity.

Deactivation of a zeolite catalyst during its use to catalyse the oligomerisation of olefins, is often believed to be a result of the formation of high boiling polymers as by-products. These by-products can remain on the catalyst and undergo further conversion to higher molecular weight polymers, which resemble heavy tars and in some cases even have the appearance of coke-like material. These materials can coat the catalyst particles and plug pores in the catalyst, thereby causing catalyst deactivation. Accordingly, the process of this invention is ideally carried out at a pressure which is sufficient to maintain a liquid or supercritical (also known as a dense) phase of hydrocarbon in contact with the catalyst. This liquid or supercritical hydrocarbon phase maintains conditions whereby the high molecular weight polymers or tar are more readily washed off the catalyst, thereby prolonging the catalyst life. The liquid or dense phase also is more effective in removing heat away from the active sites on the catalyst, thereby suppressing the formation of higher molecular weight polymers or tar.

In the practice of the process of this invention employing a zeolite catalyst, the olefin-containing feedstock is contacted with the catalyst at a temperature, pressure and period of time which are effective to result in conversion of at least a portion of the compounds in the feed to the desired oligomer products. For example, the olefin to be oligomerised may be an olefin from 3 to 9 carbon atoms, preferably from 3 to 6 carbon atoms. The contacting will generally be carried out at a temperature in the range from about 125° to about 300° C. It will be appreciated of course, that the optimum temperature will be a function of the specific reactants employed, their concentration in the feed and the catalyst employed. The contact temperature will typically be increased over the course of a run in order to maintain economically acceptable overall conversion.

The reactor temperature profile may be controlled by raising the temperature of the feed to the reactor. The temperature may be raised to, for example, 150° C. to 250° C. such as between 160° C. and 190° C. prior to introduction into the reactor, and this may be accomplished by the provision of any suitable heating means. In a preferred embodiment, the feed is heated by use of the heat generated in the reactor, such as by using the steam that has been generated to control the temperature in the shell side of the reactor, or by the heat contained in the reactor effluent, preferably by means of a feed effluent exchanger.

When the fresh feed is rich in olefin, control of conditions within the reactor tube may be affected by running low conversion per pass and a recycle of part of the unreacted olefins (mixed with the paraffins of the same carbon number) separated from the reactor product stream. The recycle ratio (weight of recycle on weight of fresh feed) may be controlled within a wide range e.g. 0.1 to 2.5, preferably 0.2 to 2.0. For example, the ratio can be low, such as 0.2 or 0.3, but can also be higher, such as 0.5, 1.0, 1.5 or 2.0. Typically, the recycle ratio will be selected depending on, for example, the fresh feed composition, the availability (or lack thereof) of another suitable diluent, and any limits on the maximum concentration of olefins in the purge stream. This purge stream contains unreacted olefins, and in one arrangement typically comprises all or part of the LPG stream coming from the distillation tower that separates the unreacted olefins and paraffins from the rest of the reaction product after the reactor; such tower is usually called the stabiliser and is often in the first position.

The above-described recycle operation permits the reactor to be operated at a relatively low per-pass conversion, but with a high overall conversion. This enables the overall desired product yield to be optimised, optionally to be maximised. By way of example the per-pass conversion may be as low as 50%, and may be achieved by steam drum pressure reduction (in the case where the temperature control fluid is water).

By fresh feed that is rich in olefin is meant, for example, in the case of a propylene feed, a feed containing at least 70 wt %, at least 85 wt %, at least 92 wt % or at least 97 wt % propylene. For a butenes feed is meant a feed containing at least 65 wt %, at least 80 wt %, at least 90 wt % or at least 94 wt % butenes. Isobutylene may be present in proportions as low as 1 wt % or 0.5 wt % or less; or alternatively in higher amounts such as up to 18 wt % or up to 22 wt % based on total fresh feed.

The temperature along the reactor tube may also be controlled by filling the reactor tube with a more active catalyst in the bottom of the tube (part near the outlet) and a less active catalyst in the upper (inlet) part of the tube. Such an arrangement is disclosed in our co-pending PCT patent application PCT/EP2005/005785.

Multiple reactors may be put in series, with the upstream reactors running with colder steam temperatures than the downstream ones. Similar to LPG recycle, this allows running high space velocities over a reactor while still reaching high overall conversions. Unlike with solid phosphoric acid catalyst (sPa), this is particularly easy to arrange with zeolite catalysts, because the pressure drop increase during the run that is typical for sPa catalyst is not observed with zeolite catalysts.

Unlike with solid phosphoric acid catalysts, the use of zeolite catalysts can provide stable operation and good selectivities at temperatures up to 300 or even 310° C. Reactor designs allowing such high temperatures also significantly extend the run length before a zeolite catalyst must be removed because of unacceptable activity.

The preferred embodiment, in which the peak temperature is controlled to a value that is no more than 50° C. above the temperature of the temperature control fluid as it exits the reactor, has enabled much improved conversion. Such control may be achieved by controlling the parameters of the temperature control fluid passing through the shell side of the reactor, such as temperature and/or pressure and/or flow rate of the fluid. This controls the removal of heat from the reactor tube and so by control of such parameters, the temperature difference between the peak temperature and the temperature of the control fluid when exiting the reactor is controlled. The techniques of the present invention are particularly applicable to operations in which the length to diameter ratio of the tube is at least 50 and in particular at least 100 more particularly from 200 to 300.

In most industrial processes such as those described previously, the refinery feed that is to be used in the hydrocarbon conversion reactions will contain impurities such as polar compounds. These impurities would be detrimental to the hydrocarbon conversion reaction and are frequently removed prior to the reaction, by for instance a water wash. In olefin oligomerisation, the feeds are frequently subject to a first alkaline wash to remove acidic polar species, such as thiols or mercaptans, followed by a weakly acidic water wash. The last water wash typically produces a feed stream which is saturated with water at the temperature at which the water wash is performed and, accordingly, the feed will preferably need to be dried for use according to the present invention.

The invention is particularly but not exclusively concerned with processes suitable for the production of $C_5$ to $C_{20}$ olefins boiling in the range of 30° to 310° C., preferably 30° to 300° C., more preferably 30° to 250° C., from propylene and/or butene and/or amylene feedstocks or their mixtures, though ethylene may be present as well. In particular the invention is concerned with the production of the olefins shown in the following table.

| | Distillation Range (° C.) ASTM D1078 | |
|---|---|---|
| Oligomer Products | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene Tetramers Or Dodecenes | 175 | 225 |
| Tridecenes | 204 | 213 |

We have found that the hexene products produced over molecular sieve catalysts generally have a higher olefin content than those produced over the conventional solid phosphoric acid catalyst, which provides a higher octane blending value of these hexene products and which makes them preferred as a gasoline component.

In a tubular reactor, the catalyst is contained in a reactor tube, generally a multiplicity of tubes which are surrounded by a circulating cooling medium. Preferably these tubes will each typically have an internal diameter of from about 25 mm to about 75 mm as previously discussed, although other diameters can also be used. The reactor may be provided with means that enable the reactor to be depressurised to flash off hydrocarbons from the catalyst. We have found that this treatment on a zeolite catalyst enables recovery of some of the activity lost during the run.

The level of di- and polyunsaturates in the feed is typically controlled to below a maximum allowable level. Preferably, the feed composition is limited to containing no more than 100 ppm by weight of acetylene and/or no more than 500 ppm of the $C_3$ polyunsaturates, methylacetylene and propadiene or allene, and/or no more than 2500 ppm or more preferably no more than 1000 ppm of butadiene. The reason for these limitations is the high reactivity and extreme coke forming properties of the di- and poly-unsaturates. We have found that, if it is necessary to use feeds containing relatively high levels of polyunsaturates, production may be sustained if the olefin concentration in the feed is reduced accordingly. This keeps the carbon deposition low, which would otherwise increase due to the heat generated by the reaction of the higher amounts of polyunsaturates present.

A conventional means for controlling the level of di- and polyunsaturates in the feed to oligomerisation is by selective hydrogenation of these compounds, preferably to their corresponding olefins, alternatively to their corresponding paraffins. The preferred choice is to perform this in the liquid phase, using a heterogeneous catalyst such as a catalyst containing palladium on a support. When the starting concentration of these compound is high, such as above 5% wt but possibly going up to 45 or 50%, the selective hydrogenation is typically performed in two stages, of which the second stage is typically the finishing or polishing reactor. If the starting level is lower, such as 3000 or 5000 ppm wt, a polishing reactor may be sufficient. Such polishing reactors are characterised by a hydrogen supply requirement that is relatively low compared to the liquid flow that is passed through the selective hydrogenation reactor. Similar situations occur when other trace components need to be removed by hydrogenation in a liquid stream, such as trace aldehydes in the production of alcohols via hydroformylation, possibly followed by hydrogenation, or in the removal of butynes in a stream of crude C4s coming from steamcracking of hydrocarbons. It is here discussed in the context of removal of methylacetylene and/or propadiene in a propylene containing stream, and/or the removal of butadiene in a stream containing C4 olefins (butene-1, cis-butene-2, trans-butene-2 and/or isobutylene).

Hydrogenation reactions typically prefer as high a partial pressure of hydrogen as is possible, in order to favorably affect the reaction rate. When the reactant to be hydrogenated is a liquid, the hydrogen gas must be dissolved in the liquid stream. This is typically achieved by injection of the hydrogen feed into the liquid stream through sparging and/or using pressure drop and turbulence to mix the two phases, and this usually upstream of the reactor. In order to achieve a target hydrogen partial pressure in the reactor, it is therefore required to supply the hydrogen feed at a significantly higher pressure to overcome the pressure drop between the hydrogen supply and the reactor. This increases hydrogen compression requirement, which is particularly costly and relatively inefficient in energy use due to the low molecular weight of the gas to be compressed.

In such liquid hydrogenation reactors, it is also important to keep the other reactant in the liquid phase as much as possible, and throughout the reactor. The overall pressure in the reactor is therefore also kept as high as possible. In many of the polishing hydrogenation reactions, the gas requirement is below its solubility limit in the liquid, and the reactor may be operated in the liquid phase only, without any gas present. This operation assures best contact of all reactants with the catalyst, and avoids a gas phase that may cause bypassing, channeling and other side effects.

We have now found that the hydrogen compression requirements can be reduced significantly in such polishing hydrogenation reactions, and in some circumstances additional compressors may be avoided. This reduces equipment complexity, and saves investment and operating expenses. Conversely, we have found that polishing hydrogenation reactions may be performed at reactor pressures that are above the available supply pressure of the hydrogen feed gas, without additional compression.

We have found that these advantages may be achieved by pressuring up the liquid feed to the hydrogenation reactor to a pressure sufficient to drive an eductor, located upstream of the reactor, wherein the hydrogen feed gas is pulled into the liquid stream from a lower pressure level and at the same time intensively mixed therewith. The pressure of the stream downstream of the eductor may be significantly above the supply pressure of the hydrogen to the eductor. The eductor is a high shear device characterised by a nozzle on the liquid inlet and a venturi throat.

As an example, a polishing reactor is considered for reducing 3000 ppm wt of about equal amounts of methylacetylene and propadiene in a propylene feed stream to oligomerisation, down to a level of 500 ppm wt or below. The hydrogen requirement is such that the feed mass rates are 3500:1 liquid to hydrogen gas. We have found that by pumping up the liquid feed to the reactor up to a pressure of 34 barg, using this extra pressure to power an eductor that takes in hydrogen supplied at a pressure 22 barg, the downstream hydrogenation reactor may still be operated at a pressure as high as 28 barg. This pressure would not be possible otherwise without the need for an extra hydrogen compressor. The reactor is able to operate below the bubble point of 55° C., without any free gas, all reactants being in the liquid phase. At a pressure of 22 barg, the reactor temperature should have been below 40° C. in order to stay below the bubble point of the reaction mixture. The reaction benefits from the higher hydrogen partial pressure and the higher operating temperature, and the reactor efficiency benefits from the absence of any vapor phase and from the enhanced mixing of hydrogen and liquid feed upstream of the reactor.

The olefin feed to the reactor is generally a mixture of a reactive olefin and an unreactive diluent, which is typically an alkane, preferably having the same carbon number as the olefin. This has often required the expensive addition of diluent to an olefin containing refinery feed. Typically the diluent may be additional amounts of the alkane found in the refinery feed and/or it may be provided by recycle of the unreacted material derived from the reactor. The need for diluent not only adds to the expense of the operation, but it also reduces the volumetric yield of the reaction with associated economic debits. It is therefore desirable to reduce the amount of diluent required.

The rate of heat generated by the oligomerisation reaction depends upon the concentration of the olefin in the feed. The higher the concentration of olefin, the more reactive the feed and the greater the heat that is generated. For example in the operation of tubular reactors employing phosphoric acid catalysts to oligomerise propylene containing feeds, it has been found necessary to limit the amount of olefin in the feed. This is because, despite employing cooling systems such as the steam generation mentioned previously, it has not been possible to perform extended continuous runs with feeds containing more than 50 wt % propylene. Typically is has only been possible to employ feeds containing much less than 50 wt % propylene, some processes operating at 40 wt % propylene or less.

The olefin feed may be obtained from an oxygenate stream. In this embodiment the olefin feed stream that is oligomerised is predominantly derived from an oxygenate to olefins unit; meaning that at least 50 wt % of the olefin feed, preferably at least 60 wt %, and more preferably at least 70 wt % of the olefin feed, is derived from an oxygenate to olefins unit. Such a feed stream should be low in sulphur, nitrogen and chlorine, to the extent that essentially no pretreatment will be required for removal of such components. In addition, such a feed stream should have a relatively low concentration of paraffins, compared to such sources as olefins from cracked hydrocarbons. However, such a feed stream will generally contain at least one oxygenated hydrocarbon at a level which would likely adversely impact catalytic life of the zeolite oligomerisation catalyst. Therefore, removal of such components is likely required. The benefit in using an oxygenate to olefins stream is that lower levels of inert components, such as propane and butane, are present.

The design of a tubular reactor may be improved to reduce the peak temperature. Smaller tube diameters allow easier heat dissipation from the center of the tubes to the tube walls, and provide for more heat exchange surface per unit of catalyst volume. They also allow for more tubes to be fitted in the same size shell.

Also reactor operations may contribute to a reduction of the peak temperature. Operating at lower per pass conversions, typically combined with separating and recycling part of the unreacted molecules from downstream of the process to the reactor feed, flattens the temperature profile in the reactor. This is easier when the fresh feed to the oligomerisation process contains less inerts such as alkanes, because a high overall olefin conversion may still be obtainable for the lower per pass conversion, while the olefin concentration in the reactor feed is still conveniently high so that a high reactor volume efficiency is obtained.

It is believed that use of a feed that is dry or has a low water level enables the reactor to operate at a lower temperature than has been used with previous systems that employed a hydrated feed. In particular, the lower temperature may be used at start up of a reaction run. The ability to use a lower temperature at start up contributes to the longer catalyst life or reactor run length, because in commercial operations the reaction is allowed to continue until the temperature rises to a certain level when the reaction is stopped, as above this temperature cracking, severe coke formation and rapid catalyst deactivation occurs. Typically the end of run temperature is between 260° C. to 300° C., preferably 270° C. to 290° C.

In the embodiment of the invention concerned with the presence of nitriles or organic nitrogen containing Lewis bases in the feed, the reduction in the water level may reduce or eliminate the hydrolysis of compounds such as the nitriles, which produces catalyst contaminants. Accordingly, the reduction in the water level can improve catalyst life when processing such nitrogen containing feeds. However, we have also found that the catalyst life may be further increased if the nitrile or Lewis base level itself is reduced to below 5 ppm, preferably to below 2 or 1 ppm, more preferably to below 0.2 or even 0.1 ppm by weight. This embodiment is particularly useful when the olefin feed is derived by catalytic cracking, since these feeds can have a higher nitrile content. It now has been found that nitriles may also occur in olefin feeds produced by steamcracking, in particular when the steamcracker is converting crude oil feeds derived from crude oil containing organic nitrogen compounds. Such organic nitrogen containing Lewis base compounds may also be introduced by further feed treatment processes, such as butadiene extraction.

Where the olefin feed stream is obtained by contacting an oxygenate with a molecular sieve catalyst, the oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol may include an aliphatic moiety having from 1 to 10 carbon atoms, more preferably from 1 to 4 carbon atoms. Representative alcohols include, but are not necessarily limited to, lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

A molecular sieve catalyst is used in the oxygenate to olefin reaction. Such a molecular sieve is defined as any molecular sieve capable of converting an oxygenate to an olefin compound. Examples of these molecular sieves include zeolites as well as non-zeolites, and are of the large, medium or small pore type. Small pore molecular sieves are preferred in one embodiment of this invention, however. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Suitable molecular sieves for the oxygenate to olefin reaction are described in International Publication Number WO 2004/009518.

The molecular sieve catalyst used in the present invention may be any molecular sieve that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2) or zeolites of the MTT structure type (for example H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites with the EUO structure type (for example, EU-1), or zeolites of the MFS structure (such as H-ZSM-57), or zeolites of the MWW structure (such as MCM-22 or ITQ-1 or MCM-49), or H-ZSM-48, or any member of the ferrierite structure family (such as ZSM-35). Other examples of suitable catalysts are offretites, H-ZSM-4 (MAZ structure), H-ZSM-18 (MEI structure) or zeolite Beta. Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites. The H-form of these molecular sieves are preferred because they are typically more active.

Another type of molecular sieve suitable for the process of the invention is SAPO-11, which has unidimensional 10-rings like ZSM-22 and ZSM-23.

Additionally, the catalyst can be a zeolite synthesised without addition of a template, for example, faujasites, zeolite L, mordenites, erloites and chabazites, the structures of which are contained in the 'Atlas of Zeolite Structure Types' by C. Baerlocher, W. M. Meler and D. H. Olson (published by Elsevier on behalf of the Structure Commission of the International Zeolite Association, $5^{th}$ Revision Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolites catalysts; and zeolite catalysts obtained by the addition of different elements (for example boron, iron and gallium), for example, by impregnation or cation exchange, or by incorporation during the zeolite synthesis.

Mixtures of two or more zeolites e.g. a mixture of ZSM-22 and ZSM-57 or ZSM-22 and ZSM-5 can be used as disclosed in EP 0746538 B1. Or alternatively, upon the surface of each zeolite crystal, a layer of another zeolite can be deposited as disclosed in EP 0808298 B1.

The zeolite conveniently has a crystallite size up to 5 µm, such as within the range of from 0.05 to 5 µm, for example from 0.05 to 2.0 µm, and typically from 0.1 to 1 µm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming. It is also possible to use, as is known in the art, a material in which silicon and aluminium have been replaced in whole or in part by other elements. Silicon may, for example, be replaced by germanium and/or phosphorus; and aluminium more especially by boron, gallium, chromium or iron. Materials containing such replacement lattice elements are also generally termed zeolites, and the term is used in this broader sense in this specification. The zeolites might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

In a further preferment, vacuum is applied to the oligomerisation reactor shortly after it is taken out of service. We have found that this removes residual hydrocarbons, preventing the build up of even heavier hydrocarbons and permitting easier removal of the catalyst. It has also been found beneficial to include such a flash-off or vacuum treatment in the procedures following an emergency or standby shutdown of the reactor, as it removes a significant portion of still reactive hydrocarbons from the catalyst while this is still hot. It therefore reduces coke build up by preventing condensation reactions on the catalyst. We have found that with this procedure, the catalyst in the reactor typically will retain or gain activity compared to pre-shutdown, when it is subsequently put into service again after the emergency or standby shutdown.

Selected streams can also be recycled to the reactor to effect dilution or to modify the product slate. For instance, in a propylene fed reactor, $C_6$, $C_9$ or $C_{12}$ olefin streams, fractionated downstream of the reactors, can be recycled to the reactor to modify the product slate distribution. Byproduct streams of carbon numbers other than the above, such as $C_{7-8}$ or $C_{10-11}$ mixtures, can also be recycled to reduce their production, if possible these may even be recycled to their full extinction. The feed to the reactors may also be diluted with such recycle streams. These recycle streams may be introduced in order to achieve one or more effects, e.g. to affect phase behaviour in the reactor, to improve heavies removal and hence catalyst life, to control conversion, to control the selectivity towards particular products, and to assist in control of the exotherm and therefore also the peak temperature.

A problem that may occur with tubular reactors, is that the circulation flow of the shell side temperature control fluid is not sufficiently high, particularly if this is driven by thermosyphon activity. In the case of water and steam, this means that there can be a high rate of vaporisation within the reactor on the shell side, such that much of the volume in the upper side of the reactor shell side and in the return line to the steam drum is occupied by steam vapour instead of by boiling water. This may impair the heat transfer in the upper part of the reactor tube or bundle of tubes, which makes the temperature profile inside the tube sharper and more difficult to control within the range required according to the invention. When colder boiler feed water is introduced in the steam drum below the liquid level, the temperature of the water flowing from the steam drum to the reactor shell side may become subcooled to below its boiling temperature, which also impairs heat transfer at the lower end of the tube bundle because the heat exchange is not immediately in the boiling regime. We have found that this problem may be alleviated by the solution suggested in our copending application PCT/US2006/006014 filed 21 Feb. 2006 or its priority application U.S. patent application Ser. No. 11/140,853 filed 31 May 2005.

An alternative way to control the temperature profile along a reactor tube, is to have the shell side temperature control fluid flow in co-current mode with the process fluid, which can provide the temperature control fluid at its lowest temperature close to the position where the process fluid is at its highest temperature. This may be achieved by forcing the circulation of the water from the steam drum from top to bottom on the shell side, in the case where the reactor tubes are arrayed vertically with their inlets at the top. This creates a risk of creating vapor pockets on the shell side, but this may be alleviated by providing vent tubes returning to the steam drum. It may alternatively be accomplished by having the process fluid moving upwards inside the reactor tubes while the temperature control fluid flows from bottom to top, for example by forced flow or simply driven by thermosyphon.

The start-up feed comprises an olefin and optionally a diluent. The relative proportions of the materials in this feed depend upon the nature of the olefin and the oligomerisation conditions. The reactions are strongly exothermic and accordingly a diluent such as a paraffinic or a heavy olefinic hydrocarbon is generally used. For example when the feed for a tubular reactor consists of $C_3$ olefins, we prefer that the feed contain from 40 or 42% to 60% or 65%, or 80% or 90% or 95% e.g. 48 to 52% by weight of olefins, with the balance being a paraffinic or a heavy olefinic hydrocarbon diluent, such as a $C_3$-$C_5$ refinery paraffinic stream. Such feeds may be readily available, for example they may be obtained from a catalytic cracker. Its olefin content may be reduced if needed, by e.g. recycling of unreacted paraffins or low olefinic streams found elsewhere or recovered from the reactor effluent. If butene is to be oligomerised in tubular reactors, we prefer to use a feed containing up to 80%, more preferably up to 70% or up to 60% olefins, e.g. from 50% to 70% olefins.

The materials obtained from the process of the present invention will generally be a mixture of desired olefin oligomers, unreacted olefins, diluent (if any is used), possibly water and other impurities. The materials are therefore separated, generally by fractional distillation primarily into the olefin oligomers, the unreacted olefins and, if present, the diluent. The unreacted olefins and diluents may be recycled to the oligomerisation reactor. The olefin oligomers may then be purified as required for use in subsequent reactions. For example the oligomers may contain trace amounts of sulphur which may damage a hydroformylation catalyst. Accordingly, if the olefins are to be used as a feed for hydroformylation, the feed may need to be desulphurised. Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels. Furthermore the olefin oligomers themselves are frequently mixtures of oligomers of different carbon number. For example oligomerisation of a mixture of propylene, butene and amylene can result in a mixture of $C_6$ to $C_{13}$ oligomers and this mixture can then be separated by fractional distillation to obtain the oligomer or oligomer mixtures desired for a particular purpose.

The process of this invention can be used in connection with the conversion of a mixture of $C_3$ and $C_4$ olefins to gasoline blending stock by oligomerisation. In such an embodiment, the feed will be comprised of at least about 25% by weight of olefins.

The present invention is illustrated by reference to FIG. 1 which plots the progress of a run for the dimerisation of butene in a tubular reactor employing the Zeolite ZSM-57 as the catalyst. The fresh feed composition was 85 wt % n-butene, 1 wt % isobutylene and 14 wt % of a mixture of iso- and normal butane.

The reactor inlet pressure was 85 barg and the reactor feed was a mixture of about 1 part of fresh feed and 1.2 parts of recycle.

FIG. 1 shows the progress of an oligomerisation run of one reactor that lasted for 399 days. It uses as abscis scale the catalyst life, expressed in tonne of oligomer produced per tonne of catalyst present in the reactor (t/t). Against the left hand scale it shows the evolution of the temperature of the steam leaving the steam drum of the reactor and against the right hand scale it shows how about the space velocity, expressed as $h^{-1}$ or 1/h, has been changed during the run. The actual parameters fluctuated much more than shown on the figure, so the raw data were smoothened in order to show the general principle of the invention. FIG. 1 is showing i. An initial phase during which the temperature increased from 150° C. to about 230° C., which employed a high feed space velocity (at the reactor inlet) of about 11.2 wt feed/wt catalyst/hour.

ii. An intermediate phase during which the temperature remained substantially constant (from 230° C. to 250° C.), which employed a medium space velocity of about 7.2 wt feed/wt catalyst/hour.

iii. A final phase when the temperature increased again, and a low space velocity of about 4 wt feed/wt catalyst/hour was employed.

The space velocity was determined by dividing the flow to the reactor by the total weight of catalyst in the reactor.

The present invention may be used for the oligomerisation of olefins such as ethylene, propylene, butenes and amylenes to produce $C_6$ to $C_{13}$ olefins which can be used as feeds for hydroformylation reactions for the production of aldehydes and alcohols. The aldehydes may then be oxidised to produce acids or hydrogenated to produce alcohols. The alcohols may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of feedstocks which are hydroformylated in the manner described in International Publication WO2005/058787. Where the aldehydes produced by this method are hydrogenated, this may readily be accomplished by the method described in International Publication WO2005/058782, which may for example use a cuprous chrome catalyst or a sulfided Ni/Mo catalyst.

The aldehydes may be oxidized to the corresponding carboxylic acids. Both the acids and the alcohols may be esterified to esters. These esters may be plasticizer esters for PVC, such as phthalates, adipates or trimellitates, or they may be lubricant esters or lubricant additive esters such as polyol esters. A suitable esterification process is described in WO 2005/021482 or our copending application PCT/EP2006/005068, filed 24 May 2006, in which a titanium-based organometallic catalyst may be used. The oligomers may also be hydrogenated to alkanes, which may be used as low sulphur, low aromatic, low pour point hydrocarbon fluids suitable in end uses such as solvents and thinners in paints, printing inks, as stove fuels, or as process fluids or carriers in polymerization processes.

We have found that, as the reaction temperature increases throughout a particular reactor run, even when the feed olefin conversion is maintained fairly constant by the temperature ramping, changes occur in the reaction selectivities with respect to carbon number, and with respect to product isomers. The changes in isomer distribution may be observed in the average degree of branching or average branchiness within one carbon number, as defined herein before. It has been found that this may affect the quality and performance of derivatives such as the phthalate ester derived from these oligomers in their use as PVC plasticizers. Product properties such as plasticizer viscosity and volatility, and performance properties such as weight loss upon aging, plastisol viscosity and viscosity stability, migration resistance and even electrical properties may be affected as a result.

For a process with only one reactor in operation, this would lead to gradually changing product yields in the different carbon numbers, and would also lead to gradual changes of the product properties as the oligomerisation reactor run proceeds. Such changes are highly undesired for reasons of production planning, as well as for consistency in the application, of the product derived from the oligomerisation process. In combination with the current invention, whereby also the space velocity through the reactor changes throughout the run, this problem is only becoming bigger and less desired.

We have now found that this problem can be overcome by providing multiple oligomerisation reactors in parallel, operate them at different stages of catalyst life and/or reactor run, and therefore at different operating temperatures, and adapt temperatures, catalyst unloadings and the selection of what catalyst is then reloaded in a staggered way, and then blend the products from the parallel reactors, preferably before these are distilled into the individual oligomer products. We have found that this reactor staggering allows to produce a range of products with yields that may be predicted depending on feedstock choice and routing, mixing or separating individual feeds, and on choice of the molecular sieve, zeolite or other solid acid oligomerisation catalyst, and with product qualities that are relatively constant such that the derivative product properties and their performances are maintained within narrow ranges that are perfectly acceptable to the end-use.

This solution can be exemplified for octene production from a butene feedstock containing primarily n-butenes (about 94%) and only 1-2% wt isobutylene, and using H-ZSM-57 as the catalyst. During the run of a single reactor, the heptene and nonene content of the octene product moved up from 3% to close to 10% as the steam drum temperature for that reactor moved up from about 150° C. at start of run to about 300° C. at the end of run. Octene average branchiness reduced from about 1.95 to 1.55 over that same period. However, with 4 reactors in parallel, operating in staggered mode and also employing the space velocity adjustment throughout the run according to the current invention, the heptene and nonene content of the octene product from oligomerisation could be kept between the narrow range of 3.8% wt to 5.8% wt, and the average branchiness of the octenes could be kept within a narrow range of 1.65 to 1.75.

The invention claimed is:

1. A continuous process for the oligomerisation of olefins employing a molecular sieve catalyst wherein an olefin containing hydrocarbon feed, containing at least 42 wt % of propylene or butenes, is passed over a bed of the molecular sieve catalyst in a tubular reactor wherein the shell side of the reactor is cooled by a temperature control fluid and the temperature of the reaction is monitored and the space velocity of the olefin stream fed to the reactor is adjusted according to the temperature measured
   wherein when the reaction temperature gradually increases over a reaction run and reaches a period of substantially stable conditions, the space velocity of the feed is reduced once the substantially stable conditions is reached, and
   wherein when the temperature starts to increase again after the period of substantially stable conditions, the space velocity of the feed is decreased further.

2. The process according to claim 1 wherein the olefin containing hydrocarbon feed comprises organic nitrogen containing Lewis bases is below 5 ppm by weight.

3. The process according to claim 1 in which the olefin feed contains less than 30 ppm of water based on the weight of hydrocarbon in the feed.

4. The process according to claim 1 in which the peak temperature within the reactor tube is no more than 50 degrees C. above the temperature of the temperature control fluid as it exits the reactor.

5. The process according to claim 1 in which the temperature of the feed entering the reactor tube is maintained at a temperature that is not more than 80 degrees C. below the temperature of the temperature control fluid exiting the reactor.

6. The process according to claim 1 wherein the fluid material contained within the reactor tube is maintained substantially in a single phase which is either a liquid or dense phase.

7. The process according to claim 1 in which the olefin containing hydrocarbon feed to the reactor contains less than 30 ppm wt of water based on total hydrocarbon in the feed, wherein the reaction product mixture exiting the reactor is at a pressure of at least 55 barg, and wherein the shell side temperature control fluid parameters are controlled such that the peak temperature in the reactor tube is no more than 50 degrees C. above the temperature of the temperature control fluid as said fluid exits the reactor.

8. The process according to claim 1, wherein the desired per pass conversion and optionally a desired recycle amount is determined, and the reaction is started by employing a space velocity for the feed of between 10 and 12 weight of feed per weight of catalyst per hour, and the temperature of the reaction is monitored by measuring the temperature of the temperature control fluid, and the feed velocity is maintained at 10 to 12 weight of feed per weight of catalyst per hour while there is an increase day by day in temperature, and when it is observed that the temperature increase is declining towards a period of substantially stable conditions, the space velocity of the feed is reduced to a value of from 6 to 10 weight of feed per weight of catalyst.

9. The process according to claim 8, wherein when the increase in temperature is observed after the period of substantially stable conditions, the space velocity of the feed is further reduced to a value of from 4 to 6 weight of feed per weight of catalyst.

10. The process according to claim 8, wherein the olefin feed contains one or more butenes, Zeolite ZSM 57 is the catalyst, and the period during which the temperature gradually increases has a duration of from 20 to 30% of the total run time, the period during which the temperature is under substantially stable conditions has a duration of from 40 to 60% of the total run time, and the period during which the temperature increases after the period of substantially stable conditions is from 20 to 30% of the run time.

11. The process according to claim 1 wherein the shell side of the tubular reactor is cooled by a vaporising temperature control fluid, wherein a purge of liquid temperature control fluid is provided and wherein the flow of the purge of liquid fluid is maintained at 5% or lower of the supply flow of the temperature control fluid.

12. The process according to claim 1 wherein the shell side of the tubular reactor is cooled by a steam generating system including a steam pressure control system and wherein the pressure drop available over the steam pressure control system is kept below 50 bar after the reactor run has reached about 75% of its total length.

\* \* \* \* \*